United States Patent [19]

Pellegrini, Jr.

[11] 4,222,962

[45] Sep. 16, 1980

[54] PROCESS FOR PREPARING A SUBSTITUTED DIPHENOXYBENZENE

[75] Inventor: John P. Pellegrini, Jr., O'Hara Township, Allegheny County, Pa.

[73] Assignee: Gulf Research & Development Company, Pittsburgh, Pa.

[21] Appl. No.: 968,508

[22] Filed: Dec. 11, 1978

[51] Int. Cl.$^2$ .................... C07C 85/24; C07C 76/02
[52] U.S. Cl. .................................. 260/571; 568/586
[58] Field of Search ............... 260/571; 568/636, 586

[56] References Cited

U.S. PATENT DOCUMENTS

| | | | |
|---|---|---|---|
| 2,765,341 | 10/1956 | Wirth et al. | 260/571 |
| 3,140,316 | 7/1964 | Towle | 260/580 |
| 3,567,783 | 3/1971 | Brown | 568/636 |
| 3,651,151 | 3/1972 | Bridger et al. | 568/636 |
| 3,702,862 | 11/1972 | Mine et al. | 260/141 R X |
| 3,755,449 | 8/1973 | Ito et al. | 260/571 |

FOREIGN PATENT DOCUMENTS

| | | | |
|---|---|---|---|
| 1154816 | 6/1969 | United Kingdom | 260/571 |
| 1216109 | 12/1970 | United Kingdom | 260/571 |
| 1377677 | 12/1974 | United Kingdom | 260/571 |

OTHER PUBLICATIONS

Arcoria et al., "Chem. Ab.", vol. 68, Ab. No. 31031u, (1968).

*Primary Examiner*—John Doll

[57] ABSTRACT

A diaminophenoxy or a dinitrophenoxybenzene is prepared in good yield from dibromobenzene and an alkali metal salt of meta-aminophenol or meta-nitrophenol under Ullmann ether synthesis conditions at low temperatures of 115° C. to 150° C.

12 Claims, No Drawings

PROCESS FOR PREPARING A SUBSTITUTED DIPHENOXYBENZENE

This invention relates to the preparation of a dinitrophenoxy or a diaminophenoxybenzene at temperatures of about 115° to about 150° C.

The recent introduction of acetylene-terminated polyimides to produce cured reaction products which are stable at very high temperatures of 450° C. and up has created an interest and need to produce the polyimides at attractive and competitive costs. The prime difficulty in the preparation of the acetylene-terminated polyimides which are described, for example, in U.S. Pat. No. 3,845,018 and U.S. Pat. No. 3,879,349, both to Norman Bilow et al, is the preparation of the monomers which include in one instance the preparation of 1,3-bis(3-aminophenoxy)benzene (APB). This invention relates to the discovery of a low temperature technique for the production of APB.

DESCRIPTION OF THE PRIOR ART

The reaction of aromatic halogen compounds with alkali metal salts of phenols in the presence of catalytic quantities of a metal such as copper is known as the Ullmann ether synthesis. Usually, diphenylethers are made via the Ullmann synthesis by the reaction of an alkali metal salt of a dihydric phenol, e.g. disodium phenoxide, with an aryl halide, e.g. bromobenzene. Brown, however, in U.S. Pat. No. 3,567,783, suggests the reaction of phenol with meta-dibromobenzene to produce [(phenoxy)-m-phenoxylene]benzene using the Ullmann synthesis (a copper salt plus KOH) at temperatures of about 180° C. to 200° C. It is noted that the teachings of Brown are limited to phenol or certain phenoxy-substituted phenols. It was found that when amino phenols were used in the process of Brown, decomposition of the aminophenols occurred. Attempts were not made to utilize nitrophenols in view of the potential explosive hazards of these nitro compounds at the temperatures suggested by Brown.

It has now been found in accordance with the invention that compounds of the formula:

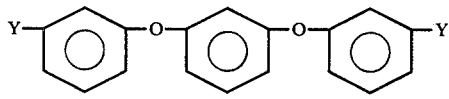

where Y is $NH_2$ or $NO_2$, can be prepared by the reaction of meta-dibromobenzene with an alkali metal salt of either meta-aminophenol or meta-nitrophenol in the presence of a solvent and an Ullmann ether synthesis catalyst and under Ullmann ether synthesis conditions including a temperature of about 115° to about 150° C. without decomposition of the amino group and without explosive hazards to result in the production of good yields of the desired amino or nitro substituted diphenoxybenzene.

The reaction occurs at the desired low temperatures utilizing an Ullmann-type ether synthesis, i.e. a metal salt such as a copper salt, and in the presence of a suitable solvent for the reaction such as pyridine.

The process of the present invention can be shown in Equation 1 below where Y can be $NH_2$ or $NO_2$.

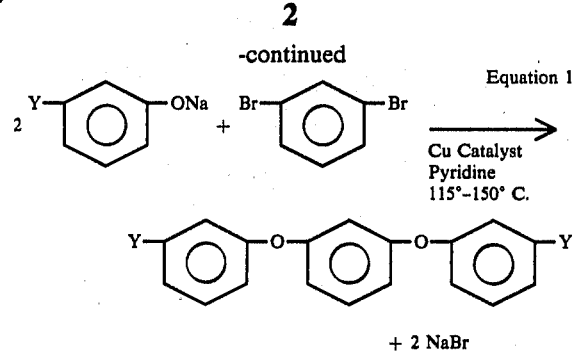

The alkali metal salt can be made in situ as per Equation 2 below:

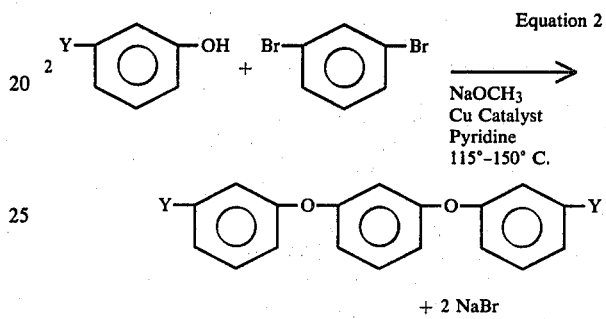

where the $NaOCH_3$ and dibromobenzene are added sequentially with intermediate removal of methanol.

The charge stocks to be utilized in the process of this invention can be obtained from any suitable source, and their preparation forms no part of this invention.

It is obvious from the stoichiometry shown in Equation 1 that the preferred molar ratio of the amino or nitrophenol to the dibromobenzene be about 2:1. However, molar ratios from 1.5:1 to 6:1 can be suitably employed in the process of this invention, albeit lower yields of the desired product should be expected at ratios below 2:1.

The process of this invention occurs under Ullmann ether synthesis conditions except for the use of the lower temperatures specified herein. The alkali metal salt can be preformed (as in Equation 1 above) or made in situ as the initial step of the process of this invention (Equation 2 above). The alkali metal salt can be prepared by the reaction of the amino or nitrophenol with an alkali metal hydroxide or alkoxide such as sodium hydroxide, potassium hydroxide, sodium methoxide, potassium methoxide, etc. Typically, the alkali metal hydroxide or alkoxide is employed in a ratio to the phenolic component of 0.90:1 to 0.98:1 to avoid an excess of base. The alkali metal hydroxide comprises sodium or potassium hydroxide; the alkali metal alkoxide may be the sodium or potassium salt of methanol, ethanol, n-propanol, isopropanol, butanol, etc. The metal salts formed are:

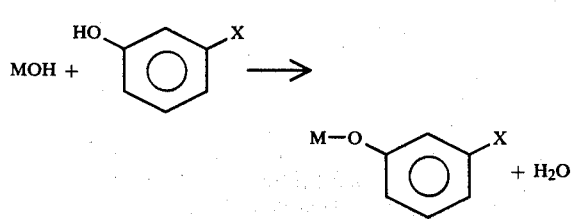

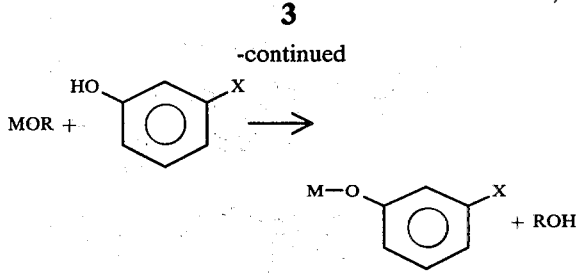

where
M = Na, K
X = NH₂, NO₂
R = CH₃, C₂H₅, C₃H₇, etc.

The alkali metal salt is preferably formed in the presence of a solvent which will azeotrope with the water or alcohol by-product for ease of removal of the water or alcohol. Benzene is typically employed. An added solvent, such as pyridine, is used for fluidity.

After the alkali metal salt is preformed or formed in situ as the initial step in the process of this invention, the Ullmann ether synthesis catalyst is added as is the dibromobenzene under Ullman ether synthesis conditions, including reaction at a temperature of 115° to 150° C. Any Ullmann type catalyst can be employed, but preferred are the copper salts such as cuprous chloride (Cu₂Cl₂) or cupric chloride (CuCl₂), albeit other soluble copper salts can be used. The catalyst concentration is usually in the range of 1-10 grams of salt per mole of phenolic reactant and is more usually from 2-5 grams per mole.

The solvent to be employed in the process of this invention to effect the ether condensation must not only dissolve the reactants but also must bring the metal catalyst, e.g. the copper catalyst, into solution as well. The particular solvent to employ is not critical, nor is the amount, so long as the reactants and catalyst are brought into solution and sufficient solvent is available to act as a heat sink to conveniently maintain the temperature within the range set forth. Typical solvents which can be utilized in the process of this invention utilizing copper salts include pyridine and quinoline as preferred solvents, as well as:
di-n-butylamine
n-propylsulfone
pyridine N-oxide
dipyridyl
2,4,6-collidine
3-ethyl-4-methylpyridine
4-ethylpyridine
2-ethylpyridine
3-ethylpyridine
2,4-lutidine
2,5-lutidine
3-picoline
2,6-lutidine
3-methyl-4-ethylpyridine
2-(3-pentyl)pyridine
4-picoline
3,4-lutidine
3,5-lutidine
2 picoline
commercial mixed picolines
3-picoline-N-oxide
2,6-lutidine-N-oxide The solvents are used in quantity sufficient to completely dissolve the substituted phenolic reactant at, or above, room temperature and give a reaction mixture which can be easily stirred.

The process of this invention is operated in the rather low temperature range of 115° to 150° C. The preferred reaction temperature is primarily a function of the type of charge stock employed. For example, when the charge stock is an alkali metal salt of meta-aminophenol, the preferred reaction temperature is from 150° to 150° C., whereas a preferred reaction temperature of 115° to 125° C. is employed when the charge stock is an alkali metal salt of meta-nitrophenol. Temperatures below about 115° C. are undesirable because the reaction rate is too sluggish. Temperatures above 150° C. are undesirable since decomposition of the charge stock may occur.

The reaction pressure is not critical and can suitably be from 10 to 100 psig, preferably from 15 to 50 psig, and most preferably, atmospheric pressure. The reaction time is dependent, of course, on the particular conditions of reaction chosen, including the charge stock, solvent and catalyst; but, in general, the reaction time is usually from 2 to 72 hours and more typically is from 8 to 24 hours.

The invention will be further described with reference to the following experimental work.

EXAMPLE 1

Into a 5-liter, 3-necked, round-bottom flask equipped with a nitrogen purge system, mechanical stirrer, condenser and Dean-Stark trap, a thermocouple and a heating mantle, were added 1500 ml of benzene, 420 grams of sodium methoxide, and a warm solution of 850 grams of meta-aminophenol, in 500 ml of pyridine. An additional 700 ml were added to rinse in the meta-aminophenol. The temperature was observed to increase to 54° to 64° C. along with the formation of a thick gray suspension, deemed to be the sodium salt of meta-aminophenol. Over a 20 to 30 minute period, the temperature was increased to reflux (80° C.) and the mixed solvents (benzene, methanol product, and pyridine) are removed continuously through the Dean-Stark trap until the overhead temperature is about 114° to 115° C. (total elapsed time of about 4 hours). At this point it was observed that the sodium salt is almost a dry cake and difficult to stir, and about 3200 ml of solvent have been removed.

The flask was cooled to 80° to 90° C. over a 30-minute period, and meta-dibromobenzene (460 grams) and 30 grams of cuprous chloride were added and rinsed in with 200 ml of pyridine. After this the heating was resumed, with removal of solvent through the Dean-Stark trap to allow the temperature to increase. When the temperature approached 120° to 124° C., the reaction mixture became fluid enough to stir easily. The pyridine was stripped (about 200 ml) until a temperature of 138° C. was achieved. The reaction mixture was maintained at about 138° C. for 24 hours.

With the heat off, the nitrogen flow was increased to strip off some pyridine solvent. Approximately 255 ml of pyridine were stripped off as the pot temperature was reduced to 90° C. 1500 ml of benzene were then added to the reaction mixture, which was stirred for 15 to 20 minutes and then suction-filtered at a temperature of about 60° to 70° C. The reaction flask and filtercake were rinsed with five 200-ml portions of hot benzene, and the rinses were added to the main filtrate which was diluted up to 4000 ml of total volume with benzene.

The 4000 ml solution of product was washed with four 2000-ml portions of 5% aqueous sodium hydroxide for the purpose of removing any excess meta-aminophenol and perhaps some pyridine. The first caustic wash was extracted with 400 ml of benzene, which was then added back to the bulk solution. Caustic washes were continued until the product was substantially colorless. The benzene solution of the aminophenoxybenzene was washed with four 2000-ml portions of water, and dried over anhydrous sodium sulfate. After filtering, the benzene solution was reduced in volume (Rotovap, water aspirator vacuum) to 3000 ml, at which point 40 to 60 grams of the colorizing carbon were added. The solution was then further decolorized by passing through a column of decolorizing carbon. The final filtrate was straw-colored and clear.

The filtrate was further reduced in volume to about 600 ml, which was poured into a suitable container and allowed to cool to room temperature with stirring. 500 ml of petroleum ether were then added gradually, and the crystallized product was suction filtered and dried overnight under vacuum at room temperature. The yield was about 370 grams of bis(m-aminophenoxy)benzene (65% of theory).

EXAMPLE 2

Into a 500-ml, 3-necked, round-bottom flask, equipped with a nitrogen purge system, mechanical stirrer, condenser and Dean-Stark trap, a thermocouple and a heating mantle, were added 50 ml of benzene, 25 ml of pyridine, sodium methoxide (5.2 grams, 0.09 mole) and a warm solution of m-nitrophenol (13.9 grams, 0.1 mole) in 50 ml of pyridine. Temperature rose from 26° C. to 36° C. as a thick red suspension formed of the sodium salt of m-nitrophenol. Over a 40-minute period, the temperature was increased to reflux (115° C.) to remove benzene, methanol product, and some pyridine. The reaction mixture was cooled to 19° C., and 1.5 g cuprous chloride and a solution of m-dibromobenzene (11.8 g., 0.05 mole) in 50 ml of pyridine was added. The reaction mixture was heated at 116° to 117° C. for 20 hours, cooled to room temperature, and poured into 400 ml of water. The water suspension was acidified with 120 ml concentrated hydrochloric acid and extracted with two 200 -ml portions of benzene. The benzene extract was washed with saturated sodium chloride solution, then with 5% sodium hydroxide solution, and then with water. The benzene extract was dried over anhydrous sodium sulfate, filtered, and the benzene removed to give bis(m-nitrophenoxy)benzene, 12.2 grams, 70% of theory.

EXAMPLE 3

In the run for this Example, m-aminophenol (2.18 grams, 0.02 mole), potassium hydroxide (0.56 gram, 0.01 mole) and 0.03 gram cuprous chloride were placed in a flask equipped with a stirrer, nitrogen inlet, thermometer, and condenser and blanketed with nitrogen. On heating, the reaction mass became fluid at about 120° C. and the potassium hydroxide dissolved. The reaction mixture was heated to 180° to 185° C. during which some foaming occurred indicating gas evolution. At 180° to 185° C., m-dibromobenzene (0.78 gram, 0.0033 mole) was added dropwise. Next, 0.45 ml of xylene was added, and reflux was maintained at 180° to 185° C. for 20 minutes. The reaction mixture was extracted with 10 ml of hot benzene, and the extract was evaporated to a volume of 1 ml. Gas chromatography showed no evidence of the presence of meta(diaminophenoxy)benzene.

EXAMPLE 4

Example 3 was repeated except the potassium salt of the m-aminophenol was formed first, followed by the addition of the cuprous chloride. Again, gas chromatography showed no evidence of the presence of the desired bis(meta-aminophenoxy)benzene.

EXAMPLE 5

Example 3 was repeated except the reaction mixture was refluxed for one hour at 180° to 185° C. Again, gas chromatography showed no evidence of the presence of the desired bis(meta-aminophenoxy)benzene.

Resort may be had to such variations and modifications as fall within the spirit of the invention and the scope of the appended claims.

I claim:

1. A process for the preparation of a compound having the formula:

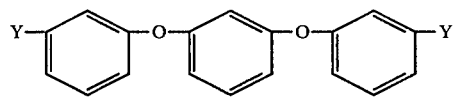

where Y is $NO_2$ or $NH_2$ which comprises:
reacting the alkali metal salt of a phenol having the formula:

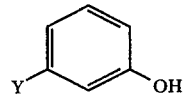

where Y is as defined, with meta-dibromobenzene in the presence of an amine solvent and an Ullmann ether synthesis catalyst and under Ullmann ether synthesis conditions including a temperature of about 115° to 150° C.

2. A process according to claim 1 wherein said Ullmann ether synthesis catalyst is a cooper salt.

3. A process according to claim 2 wherein the phenol is meta-aminophenol and the solvent is pyridine.

4. A process according to claim 2 wherein the phenol is meta-nitrophenol and the solvent is pyridine.

5. A process according to claim 3 wherein an alkali metal alkoxide is employed.

6. A process according to claim 5 wherein the copper salt is copper chloride and the alkali metal alkoxide is sodium methoxide.

7. A process according to claim 2 wherein the molar ratio of the phenol to the dibromobenzene is about 2:1.

8. A process in accordance with claim 1 wherein Y in said phenol is $NO_2$ and wherein the reaction temperature is 115° to 125° C.

9. A process in accordance with claim 1 wherein Y in said phenol is $NH_2$ and wherein the reaction temperature is 130° to 150° C.

10. A process for the preparation of a compound having the formula:

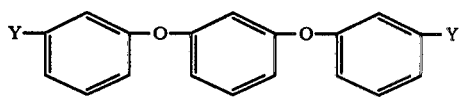

where Y is NO₂ or NH₂
which comprises:
  reacting the alkali metal salt of a phenol having the formula:

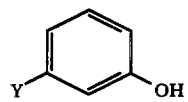

where Y is as defined, with a meta-bromoether having the formula:

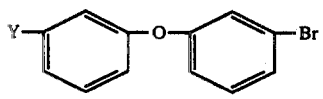

wherein Y is as defined, in the presence of an amine solvent and an Ullmann ether synthesis catalyst and under Ullman ether synthesis conditions including a temperature of 115° to 150° C.

11. A process according to claim 10 wherein said Ullmann ether synthesis catalyst is a copper salt.

12. A process according to claim 1 wherein said alkali metal salt is made in-situ by the initial reaction of said phenol with an alkali metal hydroxide or alkoxide before the addition of the dibromobenzene and Ullmann ether synthesis catalyst.

* * * * *